(12) United States Patent
Khamis et al.

(10) Patent No.: US 9,782,246 B2
(45) Date of Patent: Oct. 10, 2017

(54) SUTURE-LESS TISSUE FIXATION FOR IMPLANTABLE DEVICE

(71) Applicant: ASTORA Women's Health, LLC, Eden Prairie, MN (US)

(72) Inventors: Chaouki A. Khamis, Edina, MN (US); James A. Alexander, Excelsior, MN (US)

(*) Notice: Subject to any disclaimer, the term of this patent is extended or adjusted under 35 U.S.C. 154(b) by 0 days.

(21) Appl. No.: 15/187,744

(22) Filed: Jun. 20, 2016

(65) Prior Publication Data

US 2016/0296314 A1     Oct. 13, 2016

Related U.S. Application Data

(63) Continuation of application No. 12/983,077, filed on Dec. 31, 2010, now Pat. No. 9,393,091.

(60) Provisional application No. 61/291,379, filed on Dec. 31, 2009.

(51) Int. Cl.
| | | |
|---|---|---|
| A61F 2/00 | (2006.01) | |
| A61B 17/04 | (2006.01) | |
| A61B 17/00 | (2006.01) | |
| A61B 17/06 | (2006.01) | |

(52) U.S. Cl.
CPC ........ A61F 2/0063 (2013.01); A61B 17/0401 (2013.01); A61F 2/0045 (2013.01); A61B 2017/00805 (2013.01); A61B 2017/0427 (2013.01); A61B 2017/0464 (2013.01); A61B 2017/06176 (2013.01); A61F 2002/0072 (2013.01); A61F 2220/0016 (2013.01)

(58) Field of Classification Search
CPC ...... A61B 17/0401; A61B 2017/00805; A61B 2017/0427; A61B 2017/06176; A61B 2017/0464; A61F 2220/0016; A61F 2/0045
USPC ............................. 600/29, 30; 128/897–899
See application file for complete search history.

(56) References Cited

U.S. PATENT DOCUMENTS

| | | | | |
|---|---|---|---|---|
| 5,188,636 A * | 2/1993 | Fedotov | ................ | A61B 17/04 606/139 |
| 6,743,185 B2 * | 6/2004 | Weber | .................... | A61B 10/06 29/469.5 |
| 7,645,227 B2 * | 1/2010 | Smith | .................. | A61F 2/0045 600/30 |
| 7,951,065 B2 * | 5/2011 | Bosley, Jr. | ........ | A61B 17/06109 600/29 |
| 2002/0028980 A1 * | 3/2002 | Thierfelder | ...... | A61B 17/00234 600/37 |
| 2004/0144395 A1 * | 7/2004 | Evans | .............. | A61B 17/06066 128/885 |
| 2008/0207989 A1 * | 8/2008 | Kaleta | .............. | A61B 17/06109 600/37 |

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

A suture-less pelvic implant system and method is provided for treating pelvic conditions, such as incontinence or vaginal prolapse. The implant can include a fixation portion, which may be rectangular or suture line, having a plurality of fixation elements, e.g., barbs, extending therefrom to fixate within target pelvic tissue, such as the vaginal apex. In a sacralcolpopexy, an opposing end or anchor of the implant is fixated within the sacrum or like structure to stabilize, raise, support or reposition the vaginal apex.

17 Claims, 2 Drawing Sheets

(56) References Cited

U.S. PATENT DOCUMENTS

2009/0171143 A1* 7/2009 Chu .................... A61B 17/0401
                                              600/37
2010/0256442 A1* 10/2010 Ogdahl ............ A61B 17/06109
                                              600/30
2010/0256443 A1* 10/2010 Griguol ................ A61F 2/0045
                                              600/30
2010/0305394 A1* 12/2010 Rosenblatt ............ A61F 2/0063
                                              600/30
2011/0124954 A1* 5/2011 Ogdahl ................ A61F 2/0045
                                              600/30
2011/0301407 A1* 12/2011 Deitch ............... A61B 17/0401
                                              600/30

* cited by examiner

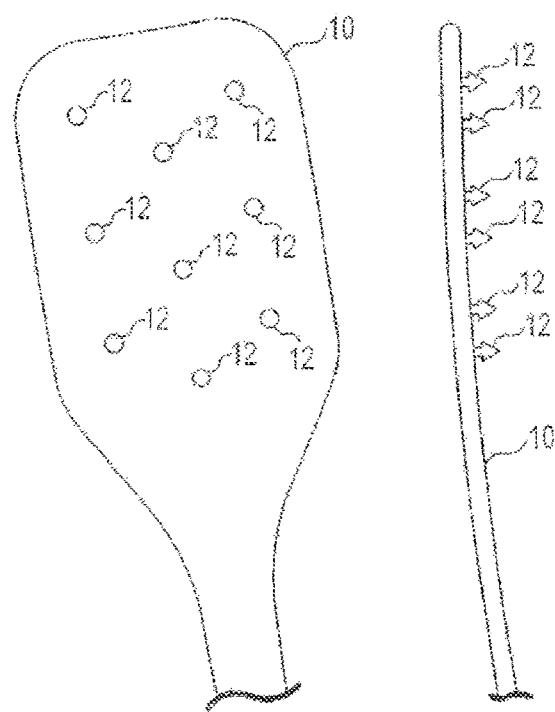
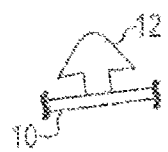  
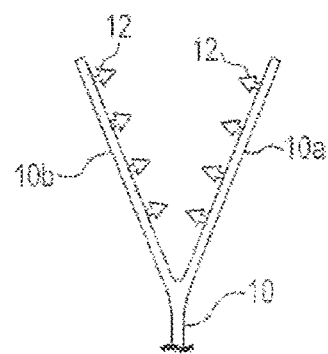

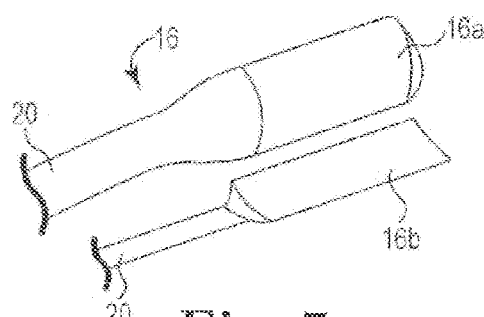
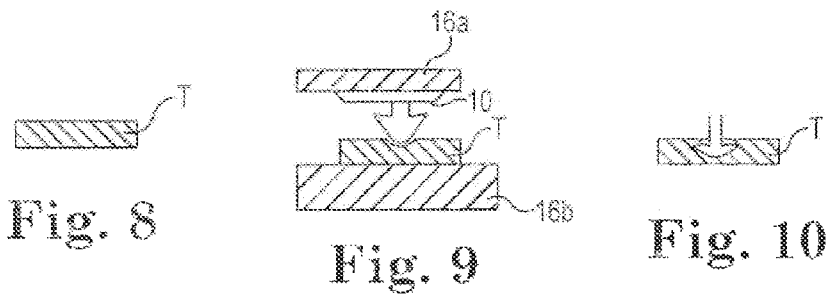
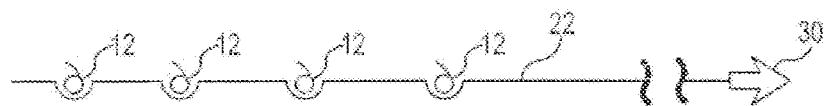
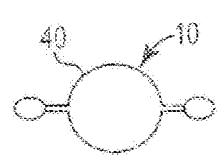
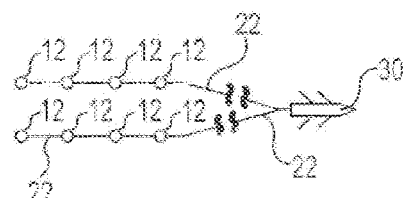
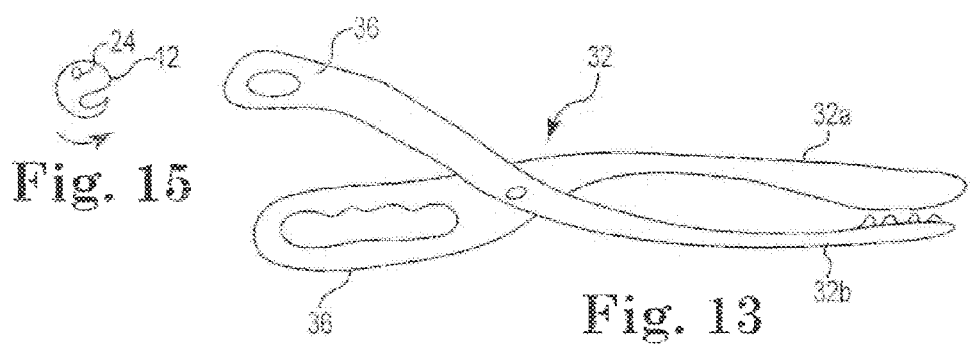

SUTURE-LESS TISSUE FIXATION FOR IMPLANTABLE DEVICE

PRIORITY

This Application is a continuation of U.S. patent application Ser. No. 12/983,077, filed Dec. 31, 2010, which claims priority to and the benefit of U.S. Provisional Application No. 61/291,379, filed Dec. 31, 2009, with each application incorporated fully herein by reference.

FIELD OF THE INVENTION

The present invention relates generally to surgical methods and apparatus and, more specifically, to suture-less surgically implantable mesh or sling devices and methods for forming and using the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

Conventional implantation of pelvic devices requires sutures. For example, in the current Sacrocolpopexy (SCP) procedure, the physician may place approximately between 5 and 16 sutures to secure the mesh to the vaginal apex. Placing these sutures is a time consuming task for the surgeon and prolongs the procedure for the patient.

There is a desire to provide an device and method for implanting a mesh implant without the use of sutures.

SUMMARY OF THE INVENTION

The present invention provides suture-less pelvic mesh implants or sling devices and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

The fixation mechanism and method in accordance with certain exemplary embodiments utilize a mesh or a line of suture material with molded or otherwise provided anchors, hooks or fixation elements, such as barbs. These fixation elements can be depth limited to prevent complete puncture or penetration of the target tissue, such as the vagina. An implantation device is also described and provides a repeatable load application to properly reach and seat the hooks.

The implant can include a fixation portion, which may be rectangular or a suture line, having a plurality of the fixation elements, e.g., barbs, extending therefrom to fixate within target pelvic tissue, such as the vaginal apex. In a sacralcolpopexy, an opposing end or anchor of the implant is fixated within the sacrum or like structure to stabilize, raise, support or reposition the vaginal apex.

BRIEF DESCRIPTION OF THE DRAWINGS

FIG. 1 is a front view of an implant having extending fixation elements in accordance with embodiments of the present invention.

FIG. 2 is a side view of the implant of FIG. 1.

FIGS. 3-5 show various implant fixation element configurations and designs in accordance with embodiments of the present invention.

FIG. 6 is a side view of a generally Y-shaped implant having extending fixation elements in accordance with embodiments of the present invention.

FIG. 7 is a partial perspective view of an insertion and fixation tool in accordance with embodiments of the present invention.

FIGS. 8-10 show various stages of deploying or inserting one or more fixation elements into tissue in accordance with embodiments of the present invention.

FIG. 11 shows a side view of a suture line implant including fixation elements and an opposing end anchor in accordance with embodiments of the present invention.

FIG. 12 shows a side view of a Y-shaped suture line implant including fixation elements and an opposing end anchor in accordance with embodiments of the present invention.

FIG. 13 shows a delivery and fixation tool in accordance with embodiments of the present invention.

FIG. 14 shows a clasp or clamp implant or implant portion in accordance with embodiments of the present invention.

FIG. 15 shows a barb or fixation element in accordance with embodiments of the present invention.

DETAILED DESCRIPTION OF PREFERRED EMBODIMENTS

The present invention is generally directed to systems and methods of deploying and attaching an implant 10. In various embodiments, the implant 10 will be adapted to provide fixation to the apex of the vagina to the sacrum or other known anatomical structures, such as that performed in a sacralcolpopexy procedure, to reposition, support or otherwise address positioning or support of the apex. The dimensions of the implant or its corresponding portions will depend upon a variety of factors including the intended surgical uses.

For a sacralcolpopexy procedure, the dimensions of the implant 10 are at least sufficient to extend from the sacrum to the vaginal apex with additional size to account for the imprecision associated with the range of human anatomy sizes and for a small amount of slack. In one embodiment, the maximum width of the implantable article is between about 1 and 6 centimeters, the overall length is between about 10 and 20 cm, and the thickness is between about 0.020 and 0.1 inches. Other dimensions are also envisioned for use with the present invention in accordance with the description and details of the fixation devices and methods provided herein. Certain embodiments of the implant 10 can be constructed of a generally flexible or semi-flexible polymer or mesh material. Relatively flexible implants 10 can be employed to contour or conform to the shape of the target fixation tissue, e.g., apex of the vagina.

Various systems, devices and methods are envisioned for use with the present invention, including those disclosed in U.S. Pat. Nos. 7,500,945, 7,407,480, 7,351,197, 7,347,812, 7,303,525, 7,025,063, 6,884,212, 6,691,711, 6,648,921, 6,612,977, and 6,541,828, International Patent Publication Nos. WO 2008/057261 and WO 2007/097994, and U.S. Patent Publication Nos. 2008/0132754, 2002/151762 and 2002/147382. Accordingly, the above-identified disclosures and references are fully incorporated herein by reference in their entirety.

This present invention includes tools and methods for suture-less approaches to tissue fixation—e.g., fixation to the vagina or vaginal apex. Namely, while sutures may be included to construct one or more portions of the implant, the sutures are not sewn to the tissue T as performed with conventional fixation methods. Conversely, embodiments of the present invention are directed to fixation of the implant 10, e.g., mesh implant, to vaginal apex tissue T without suturing. However, it should be understood that the present invention is applicable to the suture-less implantation of slings or mesh implants of any size or shape, and for any condition to be addressed by such an implant.

The fixation system and method in accordance with certain exemplary embodiments utilizes a mesh or a line of suture material with molded in, or otherwise attached or provided, anchor or hook-like fixation elements, such as barbs. These fixation elements can be depth limited to prevent a complete puncture or penetration of the tissue T, such as the vagina.

Sutures can be threaded onto or include the barbs in certain embodiments to further limit the amount of material required for fixation to the tissue T as compared to the other implants disclosed herein.

Referring now to FIGS. 1-6, the implant 10 includes a plurality of fixation elements or barbs 12 extending outwardly from one of the generally planar surfaces of the implant 10. These barbs 12 have a generally arrow-headed shape to facilitate insertion into the patient tissue and retention in the tissue (e.g., resistance to pullout). The barbs 12 take on a wide variety of shapes to facilitate fixation, while beneficially reducing the amount of force required to push the barbs 12 into the target tissue site. The barbs 12 can be angled, rounded, include one or more tines, and can include various other protuberances and features to facilitate fixation, e.g., FIGS. 3-5. In FIG. 15, a circular or partially circular barb element 12 includes a curved or angled hook to facilitate tissue fixation with corresponding rotation.

As shown in FIG. 6, the implant 10 can be generally defined in a Y-shaped form to provide better fixation to tissue T, such as the vaginal apex. For instance, a first portion 10a of the implant 10 can be affixed to the anterior portion of the apex, while a second portion 10b of the implant 10 can be affixed to the posterior portion of the apex. An opposing end of the implant 10 extends out for fixation within the pelvic cavity to tension or support the vagina or apex. For instance, the opposing end anchor described herein can be affixed or attached at or proximate the sacrum, or other tissue or anatomical structures such as the sacrospinous ligament, obturator membrane, and like tissues known to those of ordinary skill in the art for fixation in a sacralcolpopexy or similar procedure.

Again, the barbs can be sized and shaped to prevent complete penetration through the vaginal wall or apex T. FIGS. 8-10 depict the insertion of the barbs or tissue hooks into the patient tissue T, e.g., using a fixation tool 16. The barbs also resist shear forces from moving the mesh or implant 10 once fixated.

The fixation tool 16, such as shown in FIG. 7 can be provided to facilitate insertion of the barbs 12 into the patient tissue. Such a tool 16 ensures that a repeatable load is applied by giving the operator feedback in the vagina that the correct pressure has been reached and the anchors 12 are properly seated or engaged. The fixation tool 16 can include two opposing hingeable jaw portions 16a, 16b. A handle 20 of the fixation tool can be operated to actuate the jaw portions 16a, 16b together to press the barbs 12 into the respective target tissue. The handle 20 or another portion of the fixation tool 16 can click when fixation is complete, thereby providing audible and tactile feedback to the user.

In various embodiments, a vaginal incision can be made such that at least one of the jaw portion (16a) is positionable on a first side of the vaginal wall or apex and the second jaw portion (16b) is placed on the opposing side of the vaginal wall or apex. As such one jaw portion can be positioned outside the vagina and the other jaw portion inside the vagina to facilitate squeezing of the tool 16 to engage the barbs 12 into the tissue. In other embodiments, the fixation tool 16 can be employed to fixate the barbs within the tissue without requiring a vaginal incision.

Referring to FIGS. 11-12, a line or series of fixation elements or barbs 12 is shown along a suture line 22. The suture line 22 can include the previously disclosed opposing anchor 30. The opposing anchor 30 can include various tines or like features to facilitate fixation to the sacrum or other like tissue or anatomical structure within the pelvic cavity. The barbs 12 can be integrated with, attached or otherwise provided with the suture 22 at spaced locations along the length of the suture 22. In one embodiment, the barbs 12 can include one or more apertures or indents adapted to receive and secure to a portion of the suture 22. FIG. 12 shows an implant 10 having at least two distinct suture lines 22 extending from the anchor 30 to form a generally Y-shaped for apex fixation.

In certain embodiments, the sutured line of fixation elements or barbs 12 can be separately fixated to the tissue using the insertion and fixation tool 32 of FIG. 13. The tool 32 has an application or jaw portion (32a, 32b) where the fixation element assembly is retained (and optionally covered to facilitate movement through tissue). The tool 32 is then used to line up the fixation element assembly 10, 22, squeeze and engage it with the mesh and patient tissue, thereby securing the implant 10 to the tissue. The tool 32 and fixation element assembly 10, 22 can be sized and shaped according to the particular application. Further, the tool 32 can include one or more pivoting handle portions 36.

Referring to FIG. 14, the implant can be constructed as or include a clasp or clamp device 40. Such a device 40 can be adapted to clasp around a portion of the vagina, such as the apex, to capture and for fixation to the vagina a sacralcolpopexy procedure. Such clamps 40 can be used in conjunction with or as an alternative to the previous fixation elements described herein. The device 40 can be connected or extend to the anchor 30 described herein for fixation to the sacrum or like anatomical structure.

Various additional fixation element 12 and barb designs can be employed without departing from the scope of the present invention. For example, various motions can be employed with various alternative elements 12 to actuate fixation within the tissue (rotating, pivoting, pushing, sliding, etc.). The fixation elements 12 can be varied in size and shape within the same application or assembly. The fixation elements 12 can also have multiple retention features on each element 12.

The fixation elements or barbs 12 can be constructed or formed of any suitable material, including various compatible metals and polymers. Examples include polypropylene, polyethylene, fluoropolymers or like compatible materials.

Numerous modifications and variations of the present invention are possible in light of the teachings herein. It is therefore to be understood that within the scope of the appended claims, the invention may be practiced other than as specifically described herein.

The invention claimed is:

1. A method of performing a sacralcolpopexy procedure in a patient, comprising:
providing an implant having a first portion, a second portion, and a third portion, the first portion, the second portion and the third portion, collectively, defining a generally Y-shaped construct, the first portion having a plurality of fixation elements spaced along at least a portion of a length of the first portion, and wherein an anchor is coupled to the third portion;
providing a fixation tool having a first jaw portion and a second jaw portion;
attaching the first portion of the implant to first bodily tissue using the fixation tool, wherein the attaching the first portion of the implant includes:
inserting the first portion of the implant proximate to the first bodily tissue;
inserting the fixation tool within a pelvic cavity of the patient including placing the first jaw portion on a first side of the vaginal wall that is inside a vagina of the patient and placing the second jaw portion on a second side of the vaginal wall that is outside the vagina of the patient;
manipulating the first jaw portion and the second jaw portion to force the plurality of fixation elements into the first bodily tissue;
attaching the second portion of the implant to second bodily tissue; and
attaching the anchor to third bodily tissue.

2. The method of claim 1, wherein the second portion includes a plurality of fixation elements spaced along at least a portion of a length of the second portion.

3. The method of claim 1, wherein the first jaw portion and the second jaw portion of the fixation tool are hingably connected.

4. The method of claim 1, wherein forcing the plurality of fixation elements into the first bodily tissue includes forcing the plurality of fixation elements into the first bodily tissue without completely penetrating through the first bodily tissue.

5. The method of claim 1, wherein the anchor is attached to a sacrum of the patent.

6. The method of claim 1, wherein the implant is a mesh implant.

7. The method of claim 1, wherein the plurality of fixation elements are generally arrow-shaped barb members.

8. The method of claim 1, wherein the plurality of fixation elements are angled barb members.

9. The method of claim 1, wherein the plurality of fixation elements are curved barb members.

10. A method of performing a sacralcolpopexy procedure in a patient, comprising:
providing an implant having a first portion, a second portion, and a third portion, the first portion, the second portion, and the third portion, collectively, defining a Y-shaped construct, the first portion having a plurality of fixation elements spaced along at least a portion of a length of the first portion;
providing a fixation tool having a first jaw portion and a second jaw portion;
attaching the first portion of the implant to an anterior portion of vaginal wall tissue, wherein the attaching the first portion of the implant includes:
inserting the first portion of the implant proximate to the anterior portion;
inserting the fixation tool within a pelvic cavity of the patient including placing the first jaw portion on a first side of the vaginal wall tissue that is inside a vagina of the patient, and placing the second jaw portion on a second side of the vaginal wall tissue that is outside the vagina of the patient;
manipulating the fixation tool by moving the first and second jaw portions toward each other to force the plurality of fixation elements into the anterior portion;
attaching the second portion of the implant to a posterior portion of the vaginal wall tissue; and
attaching the third portion of the implant to a sacrum of the patient.

11. The method of claim 10, wherein the second portion of the implant includes a plurality of fixation elements spaced along at least a portion of a length of the second portion.

12. The method of claim 10, wherein the first jaw portion and the second jaw portion of the fixation tool are hingably connected.

13. The method of claim 10, wherein forcing the plurality of fixation elements into the anterior portion of the vaginal wall tissue includes forcing the plurality of fixation elements into the anterior portion of the vaginal wall tissue without completely penetrating through the vaginal wall tissue.

14. The method of claim 10, wherein providing the implant further includes providing the implant constructed at least in part of a suture line.

15. The method of claim 10, wherein the plurality of fixation elements are generally arrow-shaped barb members.

16. The method of claim 10, wherein the plurality of fixation elements are angled barb members.

17. The method of claim 10, wherein the plurality of fixation elements are curved barb members.

* * * * *